(12) United States Patent
Guo et al.

(10) Patent No.: US 10,828,164 B2
(45) Date of Patent: Nov. 10, 2020

(54) ILIAC PROSTHESIS

(71) Applicant: Beijing AK Medical Co., Ltd., Beijing (CN)

(72) Inventors: Wei Guo, Beijing (CN); Caimei Wang, Beijing (CN); Tao Ji, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 67 days.

(21) Appl. No.: 16/315,659

(22) PCT Filed: Jul. 8, 2016

(86) PCT No.: PCT/CN2016/089487
§ 371 (c)(1),
(2) Date: Jan. 7, 2019

(87) PCT Pub. No.: WO2018/006429
PCT Pub. Date: Jan. 11, 2018

(65) Prior Publication Data
US 2020/0222194 A1    Jul. 16, 2020

(51) Int. Cl.
*A61F 2/30* (2006.01)
*A61B 17/70* (2006.01)

(52) U.S. Cl.
CPC ....... *A61F 2/30988* (2013.01); *A61B 17/7011* (2013.01); *A61B 17/7032* (2013.01); *A61F 2002/30205* (2013.01); *A61F 2002/30242* (2013.01); *A61F 2002/30738* (2013.01); *A61F 2002/30784* (2013.01); *A61F 2002/30985* (2013.01); *A61F 2002/30995* (2013.01)

(58) Field of Classification Search
CPC ........ A61F 2/30988; A61F 2002/30995; A61F 2002/30738; A61B 17/7011
See application file for complete search history.

(56) References Cited

U.S. PATENT DOCUMENTS

2007/0191839 A1   8/2007   Justis et al.
2015/0182268 A1   7/2015   Donner et al.

FOREIGN PATENT DOCUMENTS

CN    1709211 A    12/2005
CN    102256570 A   11/2011
(Continued)

OTHER PUBLICATIONS

The Extended European Search Report for corresponding EP patent application No. 16907933.2, dated Feb. 7, 2020.

*Primary Examiner* — Jason-Dennis N Stewart
(74) *Attorney, Agent, or Firm* — Gang Yu (57) ABSTRACT

The present disclosure provides an iliac prosthesis, comprising: a prosthesis main body, the prosthesis main body including a first end portion contacted and matched with a sacrum and a second end portion contacted and matched with an acetabulum, a first screw hole being formed in the first end portion, a first screw seat being arranged in the first screw hole, the screw-rod structure including a connecting seat and a rod body, the connecting seat being connected with the prosthesis main body, and the rod body being fixed on the connecting seat; and an anti-dropping mechanism, the anti-dropping mechanism being arranged between the prosthesis main body and the connecting seat in a clamping manner. The technical solutions of the present disclosure can effectively solve the problems of unreliable supporting and easy fatigue break of the screw-rod system in the related technology.

9 Claims, 5 Drawing Sheets

(56) References Cited

FOREIGN PATENT DOCUMENTS

| | | | |
|---|---|---|---|
| CN | 102293681 | A | 12/2011 |
| CN | 105326583 | A | 2/2016 |
| CN | 106073948 | A | 11/2016 |
| WO | 9829058 | A1 | 7/1998 |

ILIAC PROSTHESIS

TECHNICAL FIELD

The disclosure relates to the field of medical devices, and more particularly, to an iliac prosthesis.

BACKGROUND

Pelvis is a site more prone to bone tumors. Pelvic tumors can be classified into primary tumors and metastatic tumors. The former mainly are chondrosarcoma, osteosarcoma and ewing sarcoma, while the later are often seen in bone metastasis of mastocarcinoma, renal carcinoma, prostate carcinoma and lung carcinoma, etc. The pathogenesis of the pelvic tumors is concealed, the early diagnosis is difficult, and when it is found, the invasion extent has been expanded greatly. In addition, the dissection around the pelvis is complex because many important organs are adjacent to it. In this sense, an operation is difficult and has various complications, poor efficacy and high mortality rate. Currently, a hemipelvectomy or an improved hemipelvic-excision limb amputation is mainly adopted for the pelvic tumors. However, the excision of any pelvic tumor will cause a bone defect, and will interrupt the continuity of a trunk and lower limbs of a patient, so that the patient stands difficultly and walks with a load, and cannot bear any weight. Moreover, the patient feels painful in walking and the acetabulum inclines inward and moves up after long-time loaded walking. Once the pelvis inclines, a vertebral column bends laterally, and thus, the life quality of the patient is seriously decreased after the operation.

Before 1970s, most malignant bone tumors in a pelvic region need to receive the hemipelvectomy. Traditionally, the hemipelvectomy refers to simultaneously excise the pelvis with a pathological change and a lower limb at a same side, resulting in severe disability of the patient. Along with the development of auxiliary therapies such as chemotherapy and radiotherapy, the advent of advanced imaging approaches and the improvement of various operative techniques, some tumors which can be treated only by an amputation formerly also may be received with a limb salvage operation, so the disability of the patient is greatly reduced. Up to now, more than 80% of patients with the pelvic malignant tumors have received the limb salvage treatment.

Because of a complex anatomical structure of the pelvic region, the limb salvage operation for pelvic malignant bone tumors is quite challenging. A pelvic ring is composed of a sacrum, and hipbones at two sides. The hipbone at each side is composed of an ilium, an ischium and a pubis. With the wide excision of the pelvic tumors, the relatively large bone defect is generally caused, the continuity of the pelvis is interrupted and partial soft tissues at the periphery are lost. A Musculoskeletal Tumor Society comes up with type classification for pelvic tumor excision, and according to an anatomic site (ilium: I region; acetabulum area: II region; obturator area: Ill region), operation types are classified into I type (ilium excision), II type (acetabulum excision), III type (obturator excision) and IV type (sacrum involved excision). If two or more regions are excised simultaneously, an excision type is a combination of corresponding regions, for example, the ilium and the acetabulum are excised simultaneously, the operation type is the I and type, if the whole pelvis is excised, it is the I, II and III type; and if a femoral head is excised simultaneously, it is the H type (such as II H, I and II H, II and III H).

After the pelvic tumor excision, it is very critical to reconstruct the pelvic ring. In this way, the weight of the trunk may be conducted to the lower limbs. For reconstruction of the defective pelvis, methods are different depending on experience of an operator and a condition of the patient. And the common reconstruction methods are exclusion, hip joint displacement, bone fusion, structural allogenic bone transplantation, artificial prosthesis and artificial prosthesis combined allogeneic bone transplantation.

For sacrum-excised composite screw-rod system reconstruction, the reconstruction method can achieve the bearing effect in a short period, but from long-term follow-up observation, a screw-rod system has the following defects: screws and rods in the screw-rod system are easily broken, fixing screws are easily loosed, a bone is easily damaged and the patients are trapped in a state that they cannot stand and walk and cannot look after themselves and must receive a fixation operation again. Moreover, such operation has large difficulty, is very demanding on accuracy, and may cause fatal massive haemorrhage or other serious complications if there is any carelessness.

SUMMARY

Some embodiments of the present disclosure provide an iliac prosthesis, so as to solve the problems of unreliable supporting and easy fatigue break of a screw-rod system in the related technology.

To this end, an embodiment of the present disclosure provides an iliac prosthesis, including: a prosthesis main body, the prosthesis main body being of an arched structure, the prosthesis main body including a first end portion contacted and matched with a sacrum and a second end portion contacted and matched with an acetabulum, first screw hole being formed in the first end portion, the first screw hole being conical hole, a first screw seat being arranged in the first screw hole, and each of the first screw seat being provided with a spherical inner surface; a screw-rod structure, the screw-rod structure including a connecting seat and a rod body, the connecting seat being connected with the prosthesis main body, and the rod body being fixed on the connecting seat; and an anti-dropping mechanism, the anti-dropping, mechanism being arranged between the prosthesis main body and the connecting seat in a clamping manner, and the anti-dropping mechanism including first anti-dropping tentacle matched with a screw accommodated in the first screw hole.

In an exemplary embodiment, a second screw hole is formed in the second end portion; the second screw hole is a conical hole; a second screw seat is arranged in the second screw hole; and the second screw seat is provided with a spherical inner surface.

In an exemplary embodiment, the connecting seat includes: a connecting screw, one end of the connecting, screw being connected with the prosthesis main body, and the other end of the connecting screw being provided with a spherical screw head; and a rod body fixing portion configured to fix the rod body, one end of the rod body fixing portion being provided with a spherical hole matched with the spherical screw head so that the rod body fixing portion is rotatably arranged on the connecting screw.

In an exemplary embodiment, the rod body fixing portion includes a U-shaped support and a fixing cap; and the rod body is arranged between the U-shaped support and the fixing cap in a clamping manner.

In an exemplary embodiment, the prosthesis main body is of a hollow truss structure; and the prosthesis main body is prototyped by 3D printing.

In an exemplary embodiment, a second screw hole is formed in the second end portion; the second screw hole is a conical hole; a second screw seat is arranged in the second screw hole; and the second screw seat is provided with a spherical inner surface.

In an exemplary embodiment, the first end portion and/or the second end portion are/is provided with a porous structure.

In an exemplary embodiment, the first end portion and/or the second end portion are/is provided with a needlelike bump.

In an exemplary embodiment, a surface, facing toward a pelvic cavity, of the prosthesis main body is a smooth surface.

In an exemplary embodiment, the anti-dropping mechanism further includes an anti-dropping main body; the anti-dropping main body is arranged between the prosthesis main body and the connecting seat in a clamping manner; the anti-dropping mechanism further includes a second anti-dropping tentacle; the first anti-dropping tentacle and the second anti-dropping tentacle are connected with the anti-dropping main body and are extended outward; and a limiting sleeve matched with the rod body is arranged on the second anti-dropping tentacle.

By applying the technical solutions of the present disclosure, the iliac prosthesis includes the prosthesis main body, and the prosthesis main body includes the first end portion contacted and matched with the sacrum and the second end portion contacted and matched with the acetabulum. As the prosthesis main body is of an arched structure, the good mechanical property is obtained, and the internal force distribution of the structure is improved. Under the condition of bearing a relatively high stress and a relatively high shear force, the rigidity of the iliac prosthesis can be maintained, so that a bone is not damaged easily. Therefore, the above-mentioned structure solves the problem that the bone is easily damaged due to the unreliable supporting and the easy fatigue break of the screw-rod system in the related technology. By applying the technical solutions of the present disclosure, the screw-rod structure includes the connecting seat and the rod body, the connecting seat is connected with the prosthesis main body, and the rod body is fixed on the connecting seat. The above structure reinforces the fixing between the prosthesis main body and the sacrum and increases the stability of the sacrum, thereby preventing the subsidence of a lumbar vertebra portion. And in addition, by applying the technical solutions of the present disclosure, the iliac prosthesis includes the anti-dropping mechanism, and the anti-dropping mechanism includes the first anti-dropping tentacle matched with the screws in the first screw hole. And the above structure can prevent the screws from dropping out from the first screw hole.

BRIEF DESCRIPTION OF THE DRAWINGS

The accompanying drawings are described here to provide further understanding of the present disclosure, and form a part of the present disclosure. The schematic embodiments and description of the present disclosure are adopted to explain the present disclosure, and do not form improper limits to the present disclosure. In the drawings.

The above accompanying drawings include the following labels:

1. a sacrum; 2. an acetabulum; 10. a prosthesis main body; 11. a first end portion; 111. a first screw hole; 12. a second end portion; 121. a second screw hole; 21. a connecting seat; 211. a connecting screw; 2111. a spherical screw head; 212. a rod body fixing portion; 2121. a U-shaped support; 2122. a fixing cap; 22. a connecting seat; 221. a connecting screw; 2211. a spherical screw head; 222. a rod body fixing portion; 2221. a U-shaped support; 2222. a fixing cap; 23. a rod body; 30. an anti-dropping mechanism; 31. a first anti-dropping tentacle; 32. an anti-dropping main body; 33. a second anti-dropping tentacle; 34. a limiting sleeve.

DETAILED DESCRIPTION OF THE EMBODIMENTS

Figure 1:
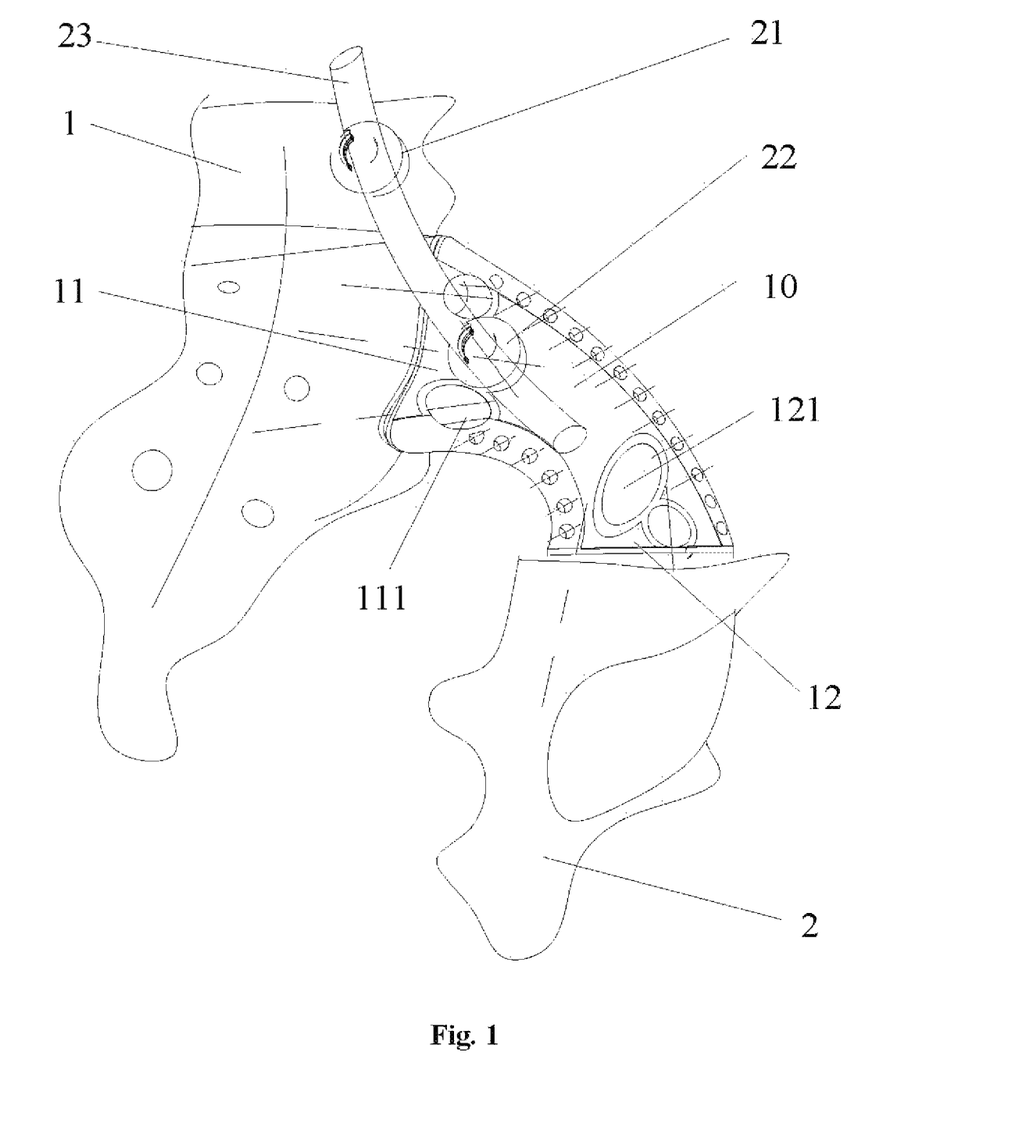
FIG. 1 depicts an assembly diagram of an angle according to an embodiment of an iliac prosthesis of the present disclosure.
Figure 2:
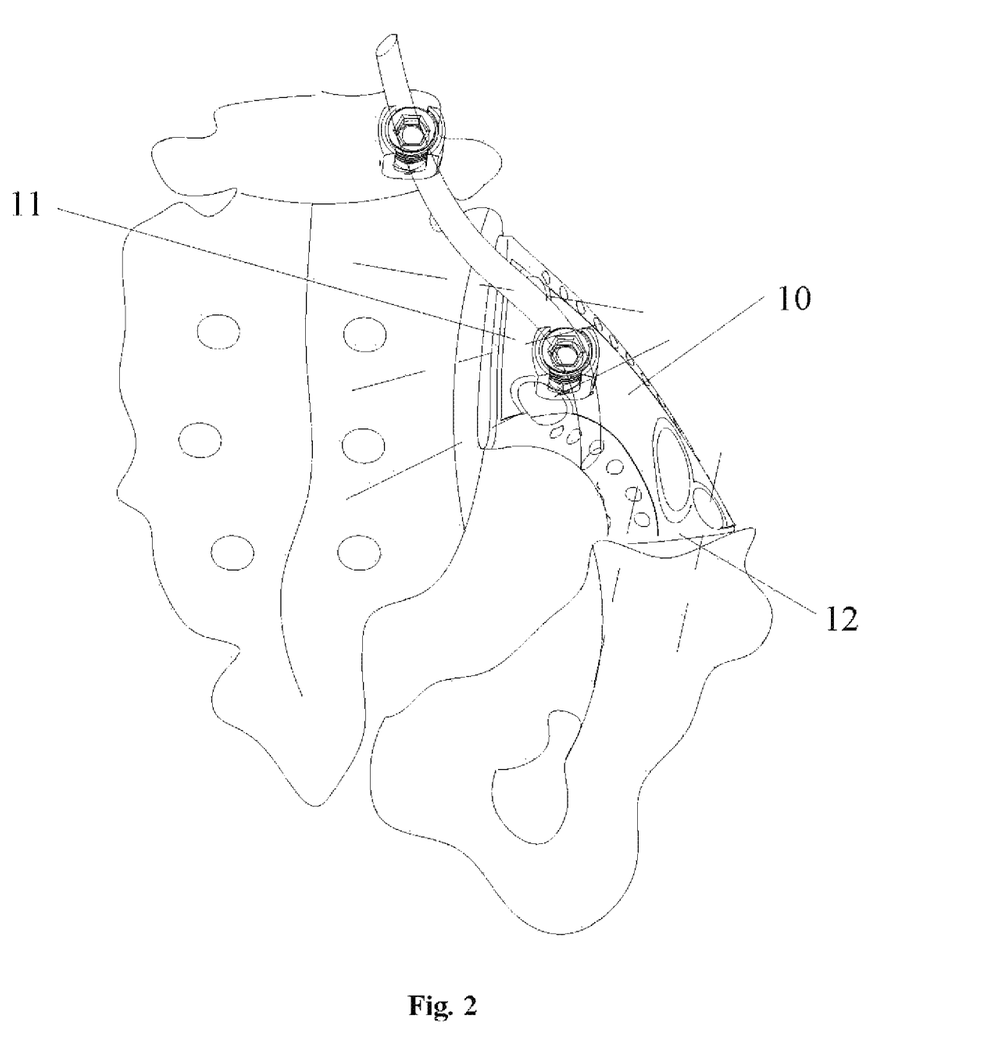
FIG. 2 depicts an assembly diagram of another angle of the iliac prosthesis in FIG. 1.
Figure 7:
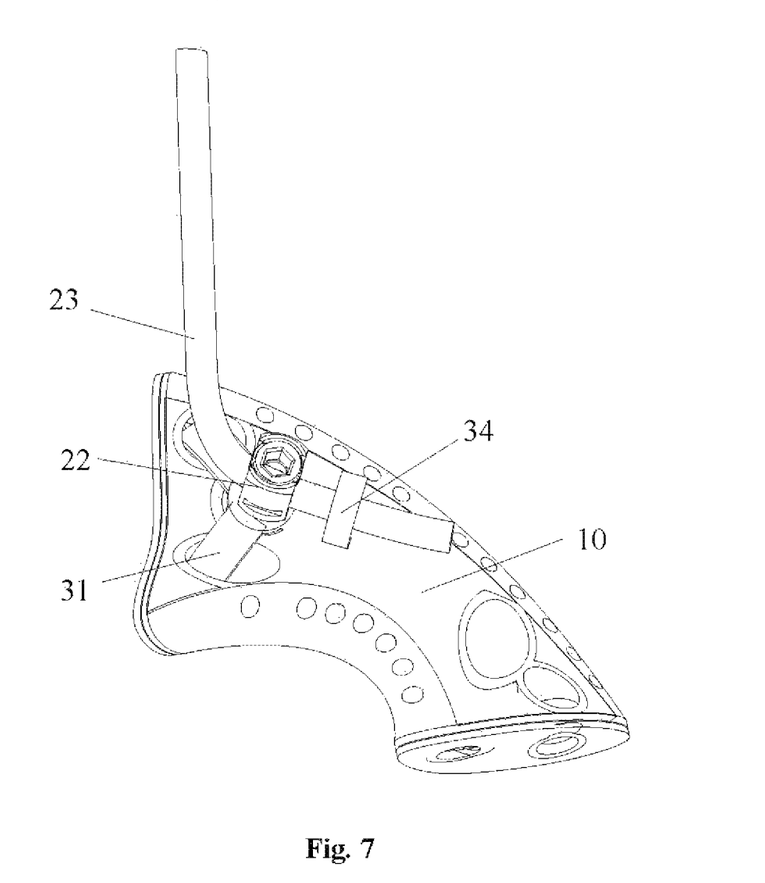
FIG. 7 depicts a three-dimensional structure schematic diagram of the iliac prosthesis provided with an anti-dropping mechanism in FIG. 1.

It is to be noted that the embodiments of the present application and the characteristics of the embodiments may be combined with each other if there is no conflict. The present disclosure is described below with reference to the drawings and embodiments in detail, As shown in FIG. 1, FIG. 2 and FIG. 7, an iliac prosthesis of the embodiment includes a prosthesis main body 10, a screw-rod structure and an anti-dropping mechanism 30, wherein the prosthesis main body 10 is of an arched structure; the prosthesis main body 10 includes a first end portion 11 contacted and matched with a sacrum 1 and a second end portion 12 contacted and matched with an acetabulum 2; a plurality of first screw holes 111 are formed in the first end portion 11; each of the first screw holes 111 is conical hole; a plurality of first screw seats are respectively arranged in the first screw holes 111; each of the first screw seats is provided with a spherical inner surface; the screw-rod structure includes a connecting seat 22 and a rod body 23; the connecting seat 22 is connected with the prosthesis main body 10; the rod body 3 is fixed on the connecting seat 22; the anti-dropping mechanism 30 is arranged between the prosthesis main body 10 and the connecting seat 22 in a clamping manner; and the anti-dropping mechanism 30 includes a plurality of first anti-dropping tentacles 31 matched with screws accommodated in the first screw holes 111.

By applying the technical solution of the present disclosure, the iliac prosthesis includes the prosthesis main body 10, and the prosthesis main body 10 includes the first end portion 11 contacted and matched with the sacrum 1 and the second end portion 12 contacted and matched with the acetabulum. As the prosthesis main body is of an arched structure, the good mechanical property is obtained, and the internal force distribution of the structure is improved. Under the condition of bearing a relatively high stress and a relatively high shear force, the rigidity of the iliac prosthesis can be maintained, so that a bone is not damaged easily. Therefore, the above-mentioned structure solves the problem that the bone is easily damaged due to the unreliable supporting and the easy fatigue break of the screw-rod system in the related technology. By applying the technical solutions of the present disclosure, the screw-rod structure includes the connecting seat 22 and the rod body 23, the connecting seat 22 is connected with the prosthesis main body 10, and the rod body 23 is fixed on the connecting seat 22. The above structure reinforces the fixing between the prosthesis main body 10 and the sacrum 1 and increases the stability of the sacrum 1, thereby preventing the subsidence of a lumbar vertebra portion. And in addition, by applying the technical solutions of the present disclosure, the iliac prosthesis includes the anti-dropping mechanism 30, and the anti-dropping mechanism 30 includes the first anti-dropping tentacles 31 matched with the screws in the first screw holes 111. And the above structure can prevent the screws from dropping out from the first screw holes 111.

Specifically, in the embodiment, an anti-dropping mechanism 30 is arranged on the prosthesis main body; the anti-dropping mechanism 30 is arranged between the prosthesis main body and the connecting seat 22 in a damping manner; and the anti-dropping mechanism 30 includes first anti-dropping tentacles 31 matched with the screws accommodated in the screw holes 111. When the connecting seat 22 is screwed tightly in use, the first anti-dropping tentacles 31 are propped against the screws accommodated in the screw holes 111. The tighter a connecting screw 221 of the connecting, seat 22 is, the greater a force that the first anti-dropping tentacles 31 are propped against the screws is. Therefore, the above structure can prevent the screws from dropping out from the first screw holes 111. In addition, it is common that the connecting screw 221 screwed to the bone are loosed in the related technology, so the anti-dropping mechanism 30 further can provide a pretightening force for the connecting seat 22 so as to prevent the looseness of the connecting seat 22.

Figure 4:
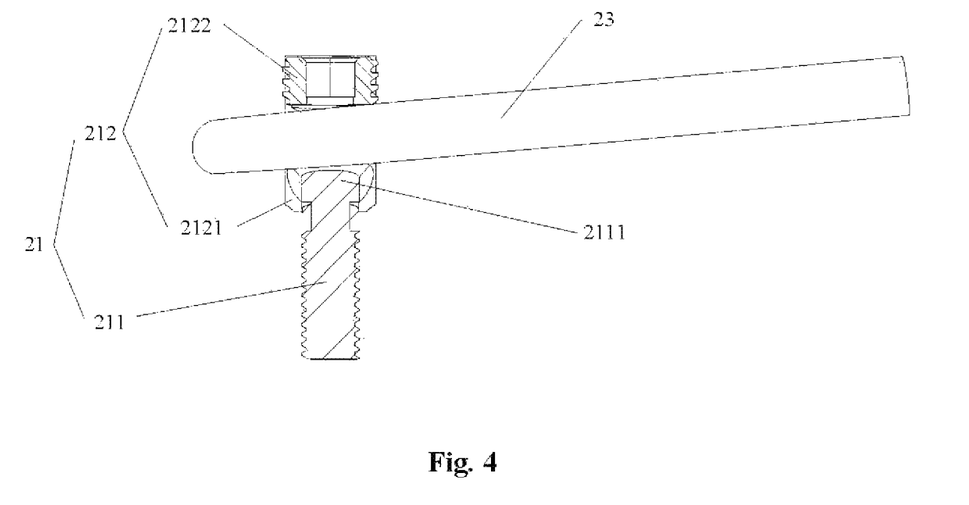
FIG. 4 depicts a schematic diagram of a longitudinal section structure of the connecting seat in FIG. 3.

As shown in FIG. 4, in the embodiment, the screw-rod structure further includes a connecting seat 21; the connecting seat 21 is connected with a lumbar vertebral body; the rod body 23 is fixed on the connecting seat 21; the connecting seat 21 includes: a connecting screw 211, one end of the connecting screw 211 being connected with the sacrum 1, and the other end of the connecting screw 211 being provided with a spherical screw head 2111; and a rod body fixing portion 212 configured to fix the rod body 23, one end of the rod body fixing portion 212 being provided with a spherical hole matched, with the spherical screw head 2111. With the above structure, the rod body fixing portion 212 can be rotatably arranged on the connecting screw 211. In this way, a doctor may adjust a position of the rod body 23 according to an actual demand, and thus, an installation position is more accurate, and an installation process is simpler.

Figure 3:
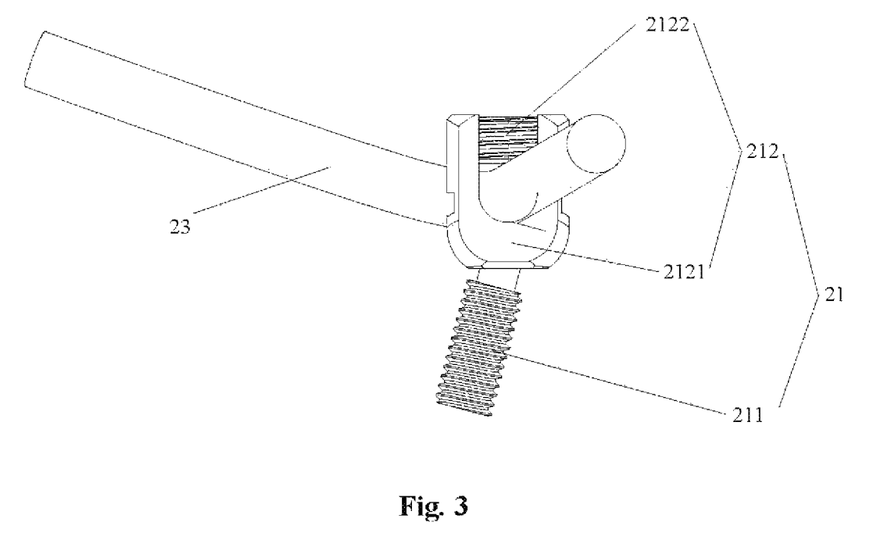
FIG. 3 depicts a three-dimensional structure schematic diagram of a connecting seat of the iliac prosthesis in FIG. 1.

As shown in FIG. 3, in the embodiment, the rod body fixing portion 212 includes a U-shaped support 2121 and a fixing cap 2122; and the rod body 23 is arranged between the U-shaped support 2121 and the fixing cap 2122 in a clamping manner. Specifically, an installation space is formed in a U-shaped inner wall of the U-shaped support 2121, and the rod body 23 is inserted into the installation space. An upper part of the U-shaped inner wall of the U-shaped support 2121 is provided with an inner screw thread, and the fixing cap 2122 is provided with an outer screw thread matched with the inner screw thread of the U-shaped support 2121. When the rod body 23 is installed, it is necessary to first enable the rod body 23 to go through the installation space and then screw the fixing cap 2122 to the U-shaped support 2121. Therefore, the above structure is simple, and convenient to install.

Figure 6:
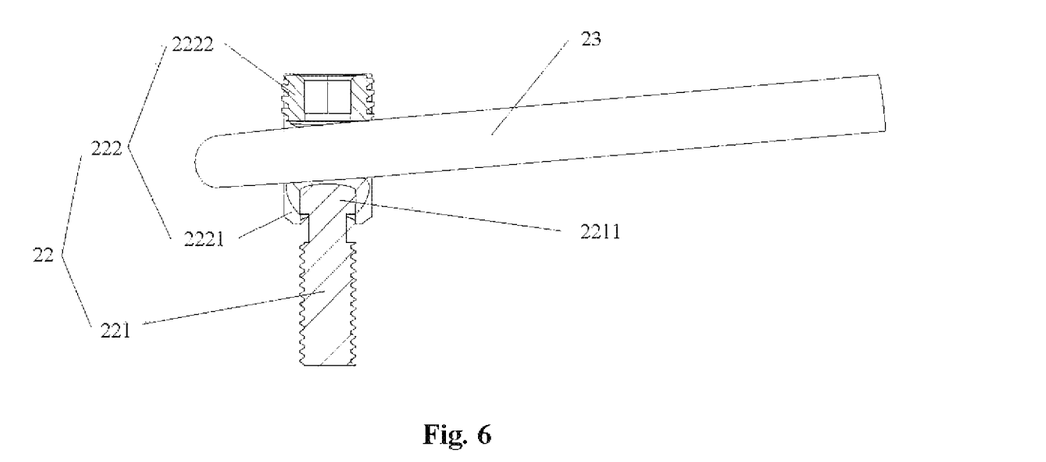
FIG. 6 depicts a schematic diagram of a longitudinal section structure of the connecting seat in FIG. 5.

As shown in FIG. 6, in the embodiment, the connecting seat 22 includes; a connecting screw 221, one end of the connecting screw 221 being connected with the prosthesis main body 10, and the other end of the connecting screw 221 being provided with a spherical screw head 2211; and a rod body fixing portion 222 configured to fix the rod body 23, one end of the rod body fixing portion 222 being provided with a spherical hole matched with the spherical screw head 2211. With the above structure, the rod body fixing portion 222 can be rotatably arranged on the connecting screw 221. In this way, a doctor may adjust a position of the rod body 23 according to an actual demand, and thus, an installation position is more accurate, and an installation process is simpler.

Figure 5:
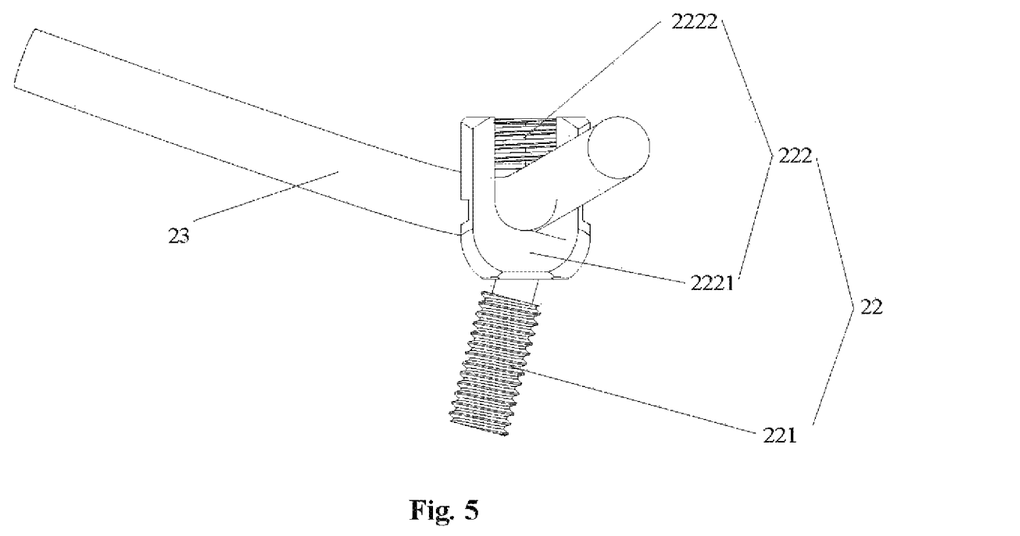
FIG. 5 depicts a three-dimensional structure schematic diagram of another connecting seat of the iliac prosthesis in FIG. 1.

As shown in FIG. 5, in the embodiment, the rod body fixing portion 222 includes a U-shaped support 2221 and a fixing cap 2222; and the rod body 23 is arranged between the U-shaped support 2221 and the fixing cap 2222 in a clamping manner. Specifically, an installation space is formed in a U-shaped inner wall of the U-shaped support 2221, and the rod body 23 is inserted into the installation space. An upper part of the U-shaped inner wall of the U-shaped support 2221 is provided with an inner screw thread, and the fixing cap 2222 is provided with an outer screw thread matched with the inner screw thread of the U-shaped support 2221. When the rod body 23 is installed, it is necessary to first enable the rod body 23 to go through the installation space and then screw the fixing cap 2222 to the U-shaped support 2221. Therefore, the above structure is simple, and convenient to install.

As shown in FIG. 1 and FIG. 2, in the embodiment, the prosthesis main body 10 is of a hollow truss structure. On one hand, the truss structure can greatly reduce the weight of the prosthesis main body 10 and improves the material utilization rate, and simultaneously further can guarantee the strength and the rigidity of the prosthesis main body 10. On the other hand, with the adoption of the above structure, the prosthesis main body 10 is closer to an adjacent skeleton, so that the bony fusion effect is better. Because anatomic reconstruction after the pelvic tumor excision needs to satisfy the accurate and complex requirements, and even further needs to satisfy the disposable and tailor-made requirements, the prosthesis main body 10 is prototyped by means of 3D printing in the embodiment. And the above process intrinsically has the characteristics of being accurate, being capable of manufacturing a complex part and being capable of personally customized.

It is to be noted that a Three-Dimensional (3D) printing rapid prototyping technology is a brand-new manufacturing technology based on a material stacking method, is different from the traditional removed material processing technology, and is also referred to as additive manufacturing (AKYCM, AKYCdditive MAKYCnufAKYCcturing). The 3D printing technology is to stack layers of a material into an entity via a rapid prototyping machine by employing 3D CAKYCD data. It is named because though different types of rapid prototyping systems have different prototyping principles and system characteristics depending on different prototyping materials used, their basic principles are the same and are to "manufacture in layers and overlap one by one", just like a "3D printer". With the rapid development of cutting-edge technologies such as manufacturing technology, digital modeling technology, numerical control technology, information technology, material science technology, chemical and biological technologies as well as the multidisciplinary close cooperation, the development of the 3D printing technology has become one of the most popular new technologies at present. The 3D printing will have a broad application prospect in the orthopedics field in future because its characteristics meet special requirements of the orthopedics. On one hand, bone tissues are a typical example of a complex structure, and it is very hard for the existing bionic technology to copy their special 3D forms and physiological functions. However, the 3D printing is just suitable for the rapid manufacturing of the complex structure and can obtain an approximately ideal bone repair material. And on the other hand, human bodies have a highly individual specificity, the traditional medical products produced in large scale and in batches cannot meet the personalized requirement and the former personalized and customized products produced by means of a manufacturing process such as mould have a high cost and a long period. Following the widespread application of a digital imaging technology in the medical field, the skeleton is an organ easiest to obtain an accurate digital image; and by combining with the skeleton and the 3D printing, the personalized medical products may be produced accurately and rapidly at a low cost. Therefore, by virtue of the 3D printing technology, an implant product with any form and an ideal biomechanical strength can be casted in a short time, making the development of personalized and customized bone implant products become true.

As shown in FIG. 1 and FIG. 2, in the embodiment, the first screw holes 111 are formed in the first end portion 11; the first screw holes 111 are conical holes; the first screw seats are arranged in the first screw holes 111; and each of the first screw seats is provided with a spherical inner surface. When the doctor needs to fix the prosthesis main body 10 onto the sacrum 1 via the screws, the screws are penetrated into the first screw hole 111 first. As the first screw holes 111 are conical holes, head portions of the screws are spherical heads and the first screw seats are provided with the spherical inner surfaces matched with the spherical heads, the screws can be rotated in a certain range, and the doctor may choose nailing directions of the screws in terms of a practical condition. With the above structure, the doctor can choose screw fixing positions according to the practical condition, so that the fixing effect between the prosthesis main body and the sacrum 1 is better. It is to be noted that dotted lines in FIG. 1 are the nailing directions of the screws. Likewise, a second screw hole 121 is formed in the second end portion 12, the second screw hole 121 is a conical hole, a second screw seat is arranged in the second screw hole 121 and the second screw seat is provided with a spherical inner surface. With the above structure, the doctor can choose screw fixing positions according to the practical condition, so that the fixing effect between the prosthesis main body and the acetabulum 2 is better.

In the embodiment, the first end portion 11 is provided with a first porous structure (not drawn in Fig.). The above structure can rapidly promote the generation of bone cells and is easily integrated with the bone (sacrum), thereby achieving the medium-long term fixing effect. Compared with the traditional operation mode, it has the characteristics of high strength, high stability and strong bone integration capability.

In the embodiment, the second end portion 12 is provided with a second porous structure (not drawn in Fig.). The above structure can rapidly promote the generation of bone cells and is easily integrated with the bone (acetabulum), thereby achieving the medium-long term fixing effect. Compared with the traditional operation mode, it has the characteristics of high strength, high stability and strong bone integration capability. And additionally, a muscle-ligament fixing hole is formed in an arc long side surface of the second end portion 12.

In the embodiment, the first end portion 11 is provided with a first needlelike bump (not drawn in Fig.). The needlelike bump has the effects of cutting and anchoring, so that the sacrum 1 is fixed with the first end portion 11 of the prosthesis main body 10 together.

In the embodiment, the second end portion 12 is provided with a second needlelike bump (not drawn in Fig.), The needlelike bump has the effects of cutting and anchoring, so that the acetabulum 2 is fixed with the second end portion 12 of the prosthesis main body 10 together.

In the embodiment, a surface, facing toward a pelvic cavity, of the prosthesis main body 10 is a smooth surface (not drawn in Fig.). The above structure can reduce a bruise of the sacral prosthesis to soft tissues such as intestinal tract in the pelvic cavity, thereby taking a certain protective effect to the soft tissues such as intestinal tract in the pelvic cavity of the patient.

Figure 8:
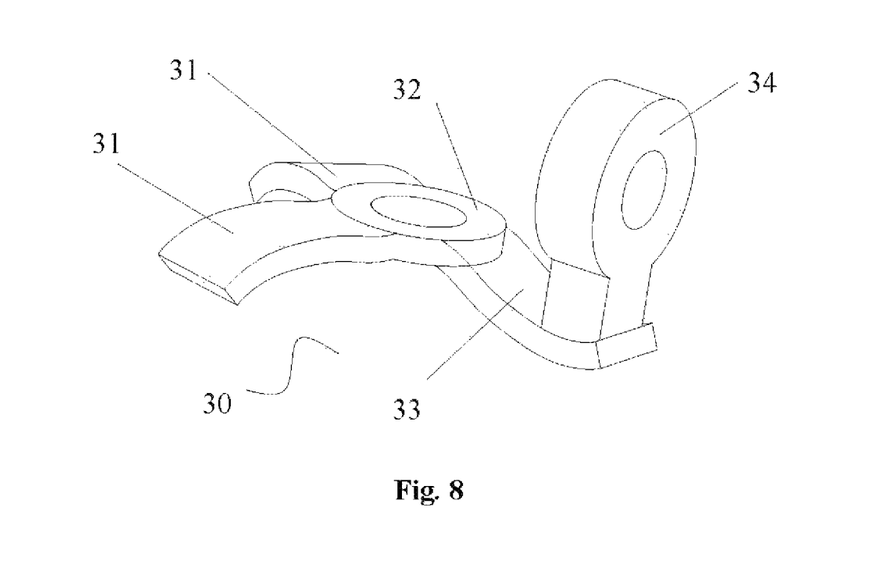
FIG. 8 depicts a three-dimensional structure schematic diagram of the anti-dropping mechanism of the iliac prosthesis in FIG. 7.

As shown in FIG. 7 and FIG. 8, in the embodiment, the anti-dropping mechanism 30 further includes an anti-dropping main body 32; the anti-dropping main body 32 is arranged between the prosthesis main body and the connecting seat 22 in a clamping manner; the anti-dropping mechanism 30 further includes a second anti-dropping tentacle 33; the first anti-dropping tentacles 31 and the, second anti-dropping tentacle 33 are connected with the anti-dropping main body 32 and are extended outward; and a limiting sleeve 34 matched with the rod body 23 is arranged on the second anti-dropping tentacle 33. Preferably, multiple first anti-dropping tentacles 31 matched with the screw holes 111 are provided. Because the multiple first anti-dropping tentacles 31 are extended outward to the screw holes 111, and the anti-dropping main body 32 is arranged between the prosthesis main body and the connecting seat 22 in a clamping manner, the anti-dropping mechanism 30 is limited and cannot be rotated. And the limiting sleeve 34 is arranged on the second anti-dropping tentacle 33 and the limiting sleeve 34 is matched with the rod body 23, so the rod body 23 is also limited and cannot be rotated. Therefore, the above structure prevents the rotation of the rod body 23, thereby increasing the stability of the system.

Preferably, the anti-dropping mechanism 30 is a leaf spring; a tail end of the second anti-dropping tentacle 33 of the leaf spring is tilted upward; and the limiting sleeve 34 is arranged at the tail end of the second anti-dropping tentacle 33.

The above description is only preferred embodiments of the present disclosure and is not intended to limit the present disclosure. Persons in the art can make various modifications and changes of the present disclosure. Any modification, equivalent replacement, or improvement made within the spirit and principle of the present disclosure shall all fall within the protection scope of the present disclosure.

What is claimed is:

1. An iliac prosthesis, comprising:
   a prosthesis main body (10), the prosthesis main body (10) being of an arched structure, the prosthesis main body (10) comprising a first end portion and a second end portion (12), the first end portion (11) is configured to contact and match with a sacrum (1), the second end portion (12) configured to contact and match with an acetabulum (2), a first screw hole (111) being formed in the first end portion (11), the first screw hole (111) being conical hole, a first screw seat being arranged in the first screw hole (111), and the first screw seat being provided with a spherical inner surface;

a screw-rod structure, the screw-rod structure comprising a connecting seat (22) and a rod body (23), the connecting seat (22) being connected with the prosthesis main body (10), and the rod body (23) being fixed on the connecting seat (22); and an anti-dropping mechanism (30), the anti-dropping mechanism (30) being arranged between the prosthesis main body (10) and the connecting seat (22) in a clamping manner, and the anti-dropping mechanism (30) comprising a first anti-dropping tentacle (31) matched with a screw accommodated in the first screw hole (111), the anti-dropping mechanism (30) further comprises an anti-dropping main body (32); the anti-dropping main body (32) is arranged between the prosthesis main body (10) and the connecting seat (22) in a clamping manner; the anti-dropping mechanism (30) further comprises a second anti-dropping tentacle (33); the first anti-dropping tentacle (31) and the second anti-dropping tentacle (33) are connected with the anti-dropping main body (32) and are extended outward; and a limiting sleeve (34) matched with the rod body (23) is arranged on the second anti-dropping tentacle (33).

2. The iliac prosthesis as claimed in claim 1, wherein a second screw hole (121) is formed in the second end portion (12); the second screw hole (121) is a conical hole; a second screw seat is arranged in the second screw hole (121); and the second screw seat is provided with a spherical inner surface.

3. The iliac prosthesis as claimed in claim 1, wherein the connecting seat (22) comprises: a connecting screw (221), one end of the connecting screw (221) being connected with the prosthesis main body (10), and the other end of the connecting screw (221) being provided with a spherical screw head (2211); and a rod body fixing portion (222), configured to fix the rod body (23), one end of the rod body fixing portion (222) being provided with a spherical hole matched with the spherical screw head (2211) so that the rod body fixing portion (222) is rotatably arranged on the connecting screw (221).

4. The iliac prosthesis as claimed in claim 3, wherein the rod body fixing portion (222) comprises a U-shaped support (2221) and a fixing cap (2222); and the rod body (23) is arranged between the U-shaped support (2221) and the fixing cap (2222) in a clamping manner.

5. The iliac prosthesis as claimed in claim 1, wherein the prosthesis main body (10) is of a hollow truss structure; and the prosthesis main body (10) is prototyped by 3D printing.

6. The iliac prosthesis as claimed in claim 1, wherein a second screw hole (121) is formed in the second end portion (12); the second screw hole (121) is a conical hole; a second screw seat is arranged in the second screw hole (121); and the second screw seat is provided with a spherical inner surface.

7. The iliac prosthesis as claimed in claim 1, wherein at least one of the first end portion (11) and the second end portion (12) is provided with a porous structure.

8. The iliac prosthesis as claimed in claim 1, wherein at least one of the first end portion (11) and the second end portion (12) is provided with a needlelike bump.

9. The iliac prosthesis as claimed in claim 1, wherein a surface, facing toward a pelvic cavity, of the prosthesis main body (10) is a smooth surface.

* * * * *